(12) United States Patent
Petyaev

(10) Patent No.: US 8,183,056 B2
(45) Date of Patent: May 22, 2012

(54) ASSAY

(76) Inventor: Ivan Mikhailovich Petyaev, Cambridge (GB)

(*) Notice: Subject to any disclaimer, the term of this patent is extended or adjusted under 35 U.S.C. 154(b) by 519 days.

(21) Appl. No.: 12/252,323

(22) Filed: Oct. 15, 2008

(65) Prior Publication Data

US 2009/0042800 A1   Feb. 12, 2009

Related U.S. Application Data

(63) Continuation of application No. 10/468,079, filed as application No. PCT/GB02/00687 on Feb. 15, 2002, now Pat. No. 7,452,731.

(30) Foreign Application Priority Data

Feb. 15, 2001 (GB) .................................. 0103765.4

(51) Int. Cl.
*G01N 33/53* (2006.01)

(52) U.S. Cl. ........ 436/512; 436/501; 436/506; 436/513; 436/518; 436/541; 435/4; 435/7.1; 435/7.93; 435/7.94; 435/7.95

(58) Field of Classification Search .................. None
See application file for complete search history.

(56) References Cited

U.S. PATENT DOCUMENTS

| 4,595,674 | A | * | 6/1986 | Tschesche et al. | ........... 514/20.4 |
| 5,807,752 | A | | 9/1998 | Brizgys et al. | |
| 6,126,933 | A | * | 10/2000 | Warne et al. | ................. 424/85.2 |
| 7,452,731 | B2 | | 11/2008 | Petyaev | |

FOREIGN PATENT DOCUMENTS

| WO | 99/32659 | 7/1999 |
| WO | 00/44733 | 8/2000 |

OTHER PUBLICATIONS

Royston "Aprotinin versus lysine analogue: The debate continues" Ann. Thoracic Surg. 65:S9-S19 (1998).
Beal & Van Dort "A comparison of the proteolytic fragmentation of immunoglobulin M from several different mammalian species" Comp. Biochem. Physiol. 71B:475-482 (1982).
Beale & Hopley "A comparison of the fragmentation of different species of mammalian immunoglobulin M by trypsin in urea" Comp. Biochem. Physiol. 76B:385-391 (1983).
Krutitskaya et al. "Autoimmune component in individuals during immune response to inactivated combined vaccine against Q fever" Acta Viologica. 40:173-177 (1996).
Medgyesi et al. "Susceptibility of human γG immunoglobulins to tryptic fragmentation" Acta Biochim. Biophys. Acad. Sci. Hung. 6:405-414 (1971).
Page et al. "Fragmentation of therapeutic human immunoglobulin preparations" Vox Sang. 69:183-194 (1995).
Patel "Rheumatoid factor—Does the patient have arthritis?" SAMJ Forum 89:742-743 (1999).
Petyaev et al. "Subsequent use of protein A and protein L for the study of the conent, distribution and composition of anti-lipoprotein immune complexes in patients with atherosclerosis" J. Submicroscop. Cytol. Pathol. 32:477 (2000).
Watanabe "Binding of Fc fragments of IgG from human and seven animal species to *Mycobacterium salivarium* cells" Microbios 76:77-84 (1993).
International Search Report for PCT/GB2002/00687 dated Mar. 25, 2003.

* cited by examiner

*Primary Examiner* — Bao Thuy L Nguyen
(74) *Attorney, Agent, or Firm* — Nixon & Vanderhye P.C.

(57) ABSTRACT

A method for determining the risk of an individual of suffering from inflammation, opportunistic infection or disruption of immunoglobulin metabolism, comprising (a) determining the level of fragmentation or modification of Fc function of immunoglobulins in a sample taken from the individual and (b) determining thereby the risk of inflammation, impaired immune response or opportunistic infection. The invention also provides the use of a trypsin inhibitor in the manufacture of a medicament for use in the treatment or prevention of a disorder associated with elevated trypsin activity which is correlated with IgG fragmentation or modification.

15 Claims, 3 Drawing Sheets

ASSAY

This application is a continuation of application Ser. No. 10/468,079, filed Nov. 7, 2003, now U.S. Pat. No. 7,452,731; which is a U.S. national stage under 35 U.S.C. 371 of International Application No. PCT/GB02/00687, filed Feb. 15, 2002; the contents of which are incorporated by reference herein.

FIELD OF THE INVENTION

The invention relates to a method for determining the level of immunoglobulin modification in a sample from an individual as a marker for inflammation, and in particular atherosclerosis in the individual. The invention also relates to the treatment of a disorder associated with elevated trypsin activity which is correlated with IgG fragmentation or modification.

BACKGROUND OF THE INVENTION

Atherosclerosis is a disease which results in narrowed arteries and decreased blood flow. The arteries become narrowed because of a build up of plaques in their inner walls. Plaques consist of a mixture of substances including cholesterol, fat, fibrous tissue, clumps of platelets and sometimes calcium.

Atherosclerosis begins early in life, but generally causes no symptoms until middle or old age. This is because it takes many years for plaques to develop and because normal arteries are much larger than they need to be. Only after an artery becomes very narrowed will blood flow be diminished enough to cause symptoms. When atherosclerosis affects arteries supplying blood to the heart, patients experience angina and claudication.

Hyperlipidaemia is a risk factor of atherosclerosis. In general, individuals with an increased level of cholesterol are prone to develop or have already developed atherosclerosis. However, although some individuals may not have an increased level of cholesterol, it does not necessarily mean that they do not suffer from atherosclerosis. Hyperlipidaemia has little diagnostic value in cardiovascular pathology since only 10-20% of the total patients with clinical complications of atherosclerosis demonstrate an elevated level of cholesterol in their plasma.

SUMMARY OF THE INVENTION

We have now determined that modification of immunoglobulins and in particular impairment of Fc function or fragmentation of immunoglobulins can be used as a marker to demonstrate the susceptibility of an individual to suffer from inflammation or an infection.

Thus, the present invention provides a method of monitoring the risk of an individual from suffering from inflammation or opportunistic infection by determining the levels of fragmentation or loss of Fc function in immunoglobulins in a sample taken from the patient. The method can therefore be used in particular to assess the immune competence of the individual and provide a useful marker of the risk of the individual suffering opportunistic infection, for example, during the course of other treatments or surgical procedures. In a preferred aspect of the invention, the method is used to determine the risk of opportunistic infection in a patient suffering from atherosclerosis.

The present invention also provides a kit for determining the risk of an individual of suffering from inflammation, opportunistic infection or disruption of immunoglobulin metabolism, which comprises means for determining the level of fragmentation or modification of Fc function of immunoglobulins in a sample taken from the individual.

We have now shown that the level of trypsin activity is elevated in patients suffering from atherosclerosis. We have also found a correlation between increased trypsin activity and the level of IgG fragmentation or damage in atherosclerosis patients' serum samples. This indicates that increased trypsin activity is one of the factors responsible for an increase in the damage to IgG in patients with clinical complications of atherosclerosis. In particular trypsin appears to be one of the main factors that causes IgG damage in cardiovascular surgery.

Accordingly, the invention provides the use of a trypsin inhibitor in the manufacture of a medicament for use in the treatment of a disorder associated with elevated trypsin activity which is correlated with IgG fragmentation or modification. The invention also provides:

a method for the treatment of a patient who has suffered or is suffering from a disorder associated with elevated trypsin activity which is correlated with IgG fragmentation or modification, which method comprises the step of administering to the patient a therapeutically effective amount of a trypsin inhibitor;

an agent for treating a disorder associated with elevated trypsin activity which is correlated with IgG fragmentation or modification comprising a trypsin inhibitor; and a trypsin inhibitor for use in the treatment of a disorder associated with elevated trypsin activity which is correlated with IgG fragmentation or modification.

DETAILED DESCRIPTION OF THE INVENTION

Assay

Figure 1:
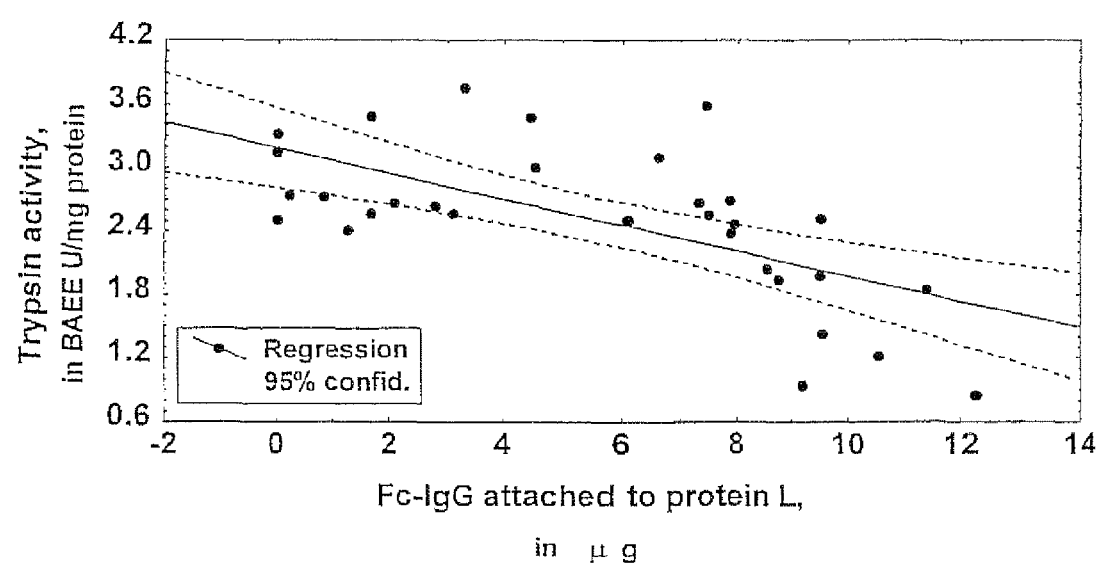
FIG. 1 shows the correlation between the level of trypsin activity and the level of IgG fragmentation in human serum from the Russian study (casewise MD deletion, r=0.6384).

The present invention provides a marker to assess immune competence of an individual. It can be used in particular to assess levels of inflammation or the susceptibility of an individual to suffer from opportunistic infection. In particular the method may be used to assess the immune competence of an individual suffering from atherosclerosis and assist in evaluating chronic inflammation in the individual.

In accordance with the method of the present invention, the level of disruption of the Fc region of immunoglobulins in a sample taken from the individual is determined. This disruption may be structural, for example the immunoglobulins have become fragmented, and in particular the Fc region or part of the Fc region of the immunoglobulin may have become detached from the remainder of the immunoglobulin molecule. Alternatively, the disruption may be functional, that is to say that the Fc region is no longer capable of being recognised, for example by no longer binding to protein A.

The method of the present invention relates in particular to a method of determining disruption of the Fc region of immunoglobulin G in a sample taken from a patient.

In accordance with the present invention, a sample is first taken from an individual. The sample may comprise a blood sample. Analysis may be carried out either on plasma or serum. Alternatively, the sample under investigation may comprise a biopsy, for example, of the arterial wall of an individual.

In accordance with the present invention, the level of disruption of immunoglobulins in the sample is determined. Quantification of the level of disruption may be measured by any suitable method. In particular the method may be used to measure the level of fragmentation of immunoglobulin, for example by measuring the levels of Fc and Fab in the sample. In the alternative, the disruption of immunoglobulins may be determined by measuring the disruption to Fc function for example through loss of binding to protein A or other proteins such as antibodies directed against the Fc portion of immuno globulin. In a preferred aspect, the levels of fragmented Fab and Fc associated with the sample are measured.

In accordance with one aspect of the invention, the sample may be contacted with an antibody sorbent. The antibody sorbent may be used to remove intact immunoglobulin from the sample, with the unbound fraction being used to monitor for fragmentation or disruption of immunoglobulins. Alternatively the nature of the immunoglobulin bound to the antibody sorbent may be determined. For example, protein A binds to immunoglobulin G via the Fc region. Thus protein A will bind whole IgG and fragments of Fc. The ratio of Fc to Fab bound to protein A provides an indication of fragmentation. Protein L binds to immunoglobulins via the k-light chain. Thus whole immunoglobulins and Fab fragments, or whole-immunoglobulin with disrupted Fc function will bind to protein L.

Any suitable antibody sorbent may be used. Examples include protein A, protein L and protein G or other proteins that bind to immunoglobulins such as peptides that bind to Ig such as kaptiv M and kaptiv GY from Tecnogen, Italy or other affinity proteins such as Arp or protein H. In a preferred aspect, the antibody sorbent for use in connection with the invention binds to immunoglobulin G. In a particularly preferred embodiment, an immunoglobulin G binding domain of protein A is used as the antibody sorbent. Protein A has been well characterised and binds to the Fc portion of IgG. In accordance with the present invention, protein A may comprise whole protein A isolated from *Staphylococcus*. Alternatively, protein A may comprise recombinant protein A. Fragments of protein A may also be provided, such fragments incorporating at least an IgG binding domain of protein A. Such fragments may comprise homologues or variants of protein A or may form hybrid proteins with other proteins, either as carriers or with other immunoglobulin binding proteins. Alternatively, protein L could be used as the antibody sorbent. Protein L has been well characterised and has been demonstrated to bind to the κ-light chains of immunoglobulins of variety of different classes. Thus, protein L will bind to Fab fragments of immunoglobulins.

The level of fragmentation or disruption of Fc function can be determined in a number of different ways. For example, using antibodies directed against the Fc portion and Fab portion, the levels of Fc and Fab in the sample may be determined or the levels of normal Fab compared to Fc which are no longer functional. For a protein A sorbent, the level of Fab provides an indication of whole, that is unfragmented immunoglobulin. The level of Fc provides an indication of whole, immunoglobulin plus fragmented Fc. The excess Fc above that expected for whole immunoglobulin based on the Fab content, provides an indication of the degree of fragmentation of Fc. In another aspect of the invention, the levels of Fab and Fc on the protein L column may be used. The Fc level provides an indication of whole immunoglobulin content. The level of Fab in excess of that expected based on the Fc/whole immunoglobulin level provides an indication of the level of fragmentation.

In a preferred aspect of the invention, the sample is first passed over an antibody sorbent. Subsequently, the sample is contacted with a second antibody sorbent. In this way, intact immunoglobulin molecules will be largely removed in the first step of the method, facilitating determination of the levels of modified immunoglobulins. For example, any immuno absorbent mentioned above may be used in the first step and subsequently the unbound fraction from that step is applied to, for example a protein L column or protein A column respectively. The levels of Fab and Fc bound to the second sorbent may be measured in the same way as described above.

The antibody sorbent can be attached to a solid phase. The sample taken from a patient can be contacted with this antibody sorbent. In a particularly preferred aspect of the invention, the antibody sorbent is provided bound to beads, and in particular to agarose beads.

The antibody sorbent may be bound to the solid support, such as beads using any suitable method. The protein bound to the solid support may be provided as fusion proteins with other proteins either to assist in attachment to the solid support or to provide other functional characteristics which might be desired. The antibody sorbent may be derivatised to assist in its attachment to the solid support such as beads. Linkers may be provided and standard coupling or conjugating techniques used.

In a preferred example of the present invention, a sample taken from a patient is split into two portions. One portion is contacted with protein A. A second portion is contacted with protein L. Alternatively, a sample which has been pre-treated with protein A is incubated with protein L. The protein A sorbent removes whole immunoglobulin from the sample. Incubation of the unbound fraction with protein L absorbs fragmented Fab of immunoglobulin G for subsequent quantification.

The antibody and fragments thereof bound to the sorbent may be collected by any suitable method. The sample may be incubated with beads to which the antibody sorbent is bound. These beads may be separated out from the remainder of the sample by centrifugation, filtration or other means such as application of a magnetic field when magnetic beads are used. For example, the sample could be passed through a non-sticky filter which does not retain free lipoproteins/cholesterol in the sample but will retain the antibody-sorbent bound to beads. Alternatively, a magnetic field could be applied to draw magnetic beads with bound antibody or fragments thereof from tire rest of the sample.

In a preferred aspect of the invention, the separation is carried out by centrifugation of the sample so that the supernatant comprising the unbound fraction of the sample can be collected. Alternatively, the beaded antibody-sorbent fraction could be collected from such centrifuged sample.

The quantities of Fc and Fab absorbed in contact with the or each antibody sorbent such as protein A or protein L can then be determined using anti-Fc antibodies or anti-Fab antibodies. In particular, the bound fraction bound to a protein A or protein L sorbent could be contacted with a suitably labelled antibody to determine the ratio of Fc to Fab fragments in each bound sample. The antibodies can be suitably labelled, using different labels selected from radio labels, fluorescent labels or other labels such as reporter enzymes which can be used in colorimetric assays. Alternatively, both antibodies can be labelled, with the same label and the assay carried out sequentially such that the level of Fc can be differentiated from the level of Fab fragments in the sample.

The ratio of Fc fragments to Fab fragments provides an indication of the degree of disruption or fragmentation of immunoglobulins. Where protein A is used, the fragmentation provides an indication of the level of fragmentation of immunoglobulin G. The levels of modification or fragmentation can be compared with samples taken from healthy individuals or samples of individuals known to be suffering from inflammation and in particular from atherosclerosis to assess the risk of opportunistic infection in the individual concerned. In addition, the method provides an indication of disruption of immunoglobulin metabolism in an individual. Thus, the method of the invention may provide a marker of the level of autoimmune disease suffered by an individual. The levels of immunoglobulin could be used to monitor the effect of a particular treatment in the individual in reducing inflammation or the auto-immune response in the individual.

Therapy

According to the invention, trypsin inhibitors may be used to prevent damage to immunoglobulins such as IgG, for example fragmentation or modification of IgG. They may also be used to prevent disruption of the normal immunoglobulin metabolism in an individual. Trypsin inhibitors may be used to treat inflammation, particularly in humans. They may be used to improve the condition of a patient who has suffered or is suffering from atherosclerosis. Trypsin inhibitors may also be used to treat or prevent complications of atherosclerosis such as angina, claudication, ischemia and myocardial infarction. Trypsin inhibitors are also useful for the treatment or prevention of post-operative or opportunistic infections, for example noscomial (hospital acquired) pneumonia, in particular dining or after cardio-vascular surgery. In a preferred embodiment of the invention, the trypsin inhibitors are used to treat individuals who have disruption or fragmentation of immunoglobulins as determined using the assay previously described.

The trypsin inhibitor may be administered to humans in various manners such as orally, intracranially, intravenously, intramuscularly, intraperitoneally, intranasally, intrademally, and subcutaneously. The particular mode of administration and dosage regimen will be selected by the attending physician, taking into account a number of factors including the age, weight and condition of the patient.

The pharmaceutical compositions that contain a trypsin inhibitor as an active principal will normally be formulated with an appropriate pharmaceutically acceptable carrier or diluent depending upon the particular mode of administration being used. For instance, parenteral formulations are usually injectable fluids that use pharmaceutically and physiologically acceptable fluids such as physiological saline, balanced salt solutions, or the like as a vehicle. Oral formulations, on the other hand, may be solids, e.g. tablets or capsules, or liquid solutions or suspensions.

Trypsin inhibitors have been isolated from lima beans, egg white, pancreatic tissues and soybean. A trypsin inhibitor may work directly on the trypsin molecule, for example by blocking its interaction with immunoglobulins. Alternatively, the trypsin inhibitor may activate natural anti-trypsin components of the blood such as alpha$_1$ antitrypsin or $\alpha_2$-macroglobulin. Increased trypsin levels or activity may also be inhibited or controlled by administering isolated anti-trypsin blood factors (such as alpha$_1$ antitrypsin and $\alpha_2$-macroglobulin) or by administering whole plasma containing these factors. The plasma may be obtained from human donors, animals or may be artificial plasma.

For the present invention, a suitable trypsin inhibitor is aprotinin. This inhibitor is a single chain polypeptide derivable from bovine lung tissues which consists of 58 amino acid residues and which has a molecular weight of 6,500 Da. Aprotinin inhibits proteolytic enzymes including trypsin and kallidinogenase. It also inhibits plasmin and plasminogen activators. It has previously been used in the treatment of haemorrhage due to hyperfibrinolysis and in some types of shock, and so has been proved to be a relatively safe and non-toxic therapeutic agent.

The amount of trypsin inhibitor that is given to a patient will depend upon a variety of factors including the condition being treated, the nature of the patient under treatment and the severity of the condition under treatment. Initially the level of trypsin activity in the patient's serum may be determined, and then an appropriate quantity of trypsin inhibitor may be administered in order to bring trypsin levels or activity back to a normal range. Typically, a patient will be given a dose of 0.01 to 500,000 kallikrein units of a trypsin inhibitor. Generally the dose will be between 1,000 and 200,000 kallikrein units. The timing of administration of the trypsin inhibitor should be determined by medical personnel. For example, a patient may receive an intravenous infusion or injection of 20,000 kallikrein units of trypsin inhibitor one to two hours before the beginning of cardio-vascular surgery. For the treatment of chronic inflammation or atherosclerosis, such a dose may be administered on a regular basis, for example daily, several times a week or weekly, as determined by the attending physician.

EXAMPLES

Materials and Methods

Most of the chemicals were from "Sigma". rProtein L was from "ACTIgen". All solutions were prepared in 0.05M phosphate buffer with 0.1 mM diethylenetriaminepentaacetic acid (DTPA), pH 7.4 unless otherwise stated. All measurements were performed in triplicate at least.

Human specimens. There were two groups of specimens of aorta from patients with clinical complications of atherosclerosis. The first was obtained from necropsy on 21 patients (age range 48-85 years, 16 male, 5 female) at Addenbrooke's Hospital in Cambridge, UK. In some cases in this group, as in the following one, more than one lesion samples was taken from the same patient. The pieces of aorta were digested by collagenase.

The second group of specimens together with samples of plasma, serum and in some cases biopsy of quadriceps femoris muscle were recovered from 11 patients (age range 53-64 years, 8 male, 3 female) during bypass surgery of the patients with an abdominal aorta stenosis at the Centre of Cardio-Vascular Surgery of the Clinical Hospital No. 1 in Rostov-na-Donu, Russia. After recovery these samples were immediately put in 30% w/v solution of NaCl and stored at 0-4° C. for 1-2 weeks prior to examination. In the control experiments it was shown that during this period the activities of such enzymes as trypsin, catalase, superoxide dismutase, glutathione peroxidase, creatine kinase and lactate dehydrogenase, together with a level of immunoglobulin (IgG) fragmentation and a degree of lipid peroxidation (concentration of malonaldehydes) did not significantly change (data not presented).

The pieces of aorta (approximately 200-400 mg wet weight) were immersed in phosphate-buffer saline (PBS) and scraped with a blunt glass rod about 8-10 times. After that no further protein could be detected in these extracts. The remaining samples were cut into about ten to twenty pieces each, placed in 5.0 ml of PBS and homogenised by a mechanical homogeniser (Ultra-Turrax) at full-power with a 15 mm probe three times for 3 seconds each with 20 second cooling intervals. In order to determine the optimum condition for the extraction of immunoglobulins (Igs) this procedure was performed with different concentrations of two non-ionic detergents, Triton X-100 and Igepal CA-630. After homogenisation the insoluble components were separated by centrifugation at 5000 g for 10 minutes and supernatants were used for analysis.

Immunoglobulin/immune complex extraction. The first step was the treatment of the analysed samples with protein A attached to cross-linked 4% beaded agarose at 37° C. for 30 minutes. After that immunoglobulins and/or immune complexes which had bound via this protein to the beads were spun down at 5000 g for 10 minutes. Supernatants were removed for the further tests. Sediments were re-suspended in PBS and these samples were centrifuged under the same regime. This washing procedure was repeated three times.

In the second step the supernatants were treated with rProtein L attached to cross-linked 4% agarose under the same conditions as described for protein A. The different ratios between proteins A/L and analysed types of material were tested to find the optimal which gives the maximum yield of immunoglobulins (see results).

In the control experiments, under the same conditions two 10% w/v suspensions of Staphylococcus aureus were used instead of protein A reagent; one the strains were Cowan strain bearing protein A, and Wood 46 strain not bearing protein A.

Immunoglobulin content and quantification. Since neither protein A nor rProtein L reagents affect alkaline phosphatase, APase, reaction themselves (data not shown), it was possible to use APase antibody conjugates for immuno-enzyme assays to measure the concentration of immunoglobulins attached to the protein A/L agarose beads. To determine IgG, IgA and IgM anti-human affinity isolated goat antibody APase-conjugates were applied. To determine subclasses of IgG mouse monoclonal appropriate antibodies (IgG class) were firstly used with the consequent application in the second stage of anti-mouse goat antibody APase-conjugates. The monoclonal anti-human IgG1 was derived from clone SG-16 mouse ascites fluid, anti-human IgG2 from clone HP-6014, anti-human IgG3 from clone HP-6047, anti-human IgG4 from SK-44. The titre of the working solutions for mouse antibodies against IgG1 was 1:2,000, against IgG2 and IgG4 was 1:1,000 and against IgG3 was 1:500. All these antibodies belonged to the mouse IgG1 isotype. The goat conjugates used were pre-absorbed with bovine and human proteins and used in the titre of 1:10,000.

To exclude the binding of these antibodies directly with protein A/L and binding of goat APase conjugates with protein A, all analysed samples were preliminarily incubated with bovine IgG in the ratio 2.5 mg of the immunoglobulin per 0.1 ml of the sorbent. The APase conjugates had no cross-reactivity with bovine IgG. Although the binding of these conjugates to rProtein L was much lower than to protein A, the level of this binding, either in direct or non-direct method, was always measured in control experiments and deducted when the level of immunoglobulins was calculated in the analysed samples.

In order to determine the quantity of immunoglobulins attached to the sorbent the titration of commercial human IgG, IgA and IgM with protein A and rProtein L was performed under the same conditions as for the tested specimens.

Each stage of incubation of the protein A/L extracts with the appropriate antibodies lasted 30 minutes at 37° C., accompanied by repeating three times the centrifugation of the samples at 5,000 g for 10 minutes and their re-suspension in PBS. To determine the amount of APase conjugate attached to the sorbent p-Nitrophenyl Phosphate (pNPP), as a substrate for alkaline phosphatase, was used. This substrate was added directly to the beaded conjugate, mixed well and incubated at ambient temperature for 60 minutes. After mat all samples were centrifuged for 10 minutes at 5,000 g, supernatants were collected and analysed at λ400 nm. In some cases the analysed samples were further diluted in order to make the level of their absorption between 0.03 and 1.0 where it has a linear character.

Immunoglobulin/immune complexes elution from protein A/L reagents. Immunoglobulins (free or in a form of immune complexes) attached to either protein A or rProtein L were delipidated by 5% of Igepal CA-630. After 5 times washing in PBS and centrifuging at 5,000 g for 10 minutes these samples were re-suspended and incubated in 0.01M acetate buffer pH 2.5 for 30 minutes. Apparently this procedure affects neither covalently bound protein A nor rProtein L to agarose. After a further centrifugation under the same regime, supernatants containing immunoglobulins and, perhaps, their antigens were collected and pH was restored to 7.4.

Protein concentrations. Protein concentration of the extracts was determined by Peterson's modification of the micro-Lowry method, which utilises sodium dodecylsulfate to facilitate the dissolution of relatively insoluble lipoproteins. Bovine serum albuimn was used for the calibration curve.

Example 1

Immunoglobulin Composition of the IAM Extracted from Atherosclerotic Lesion

The immunoglobulin profile of the material extracted by both protein A and subsequently by protein L reagents from the surface of the advanced lesion and from the homogenate of its core is presented in Table 1. According to this the main immunoglobulin class in these extracts is IgG. Most surprising was the finding of this protein in the material which had been preliminarily exhausted by an excessive amount of protein A. 46% of the total fraction of IgG in PBS extract and 32% in Triton X-100 homogenate were unable to interact with protein A but not protein L.

TABLE 1

Characterisation of immunoglobulins in advanced atherosclerotic plaque (patient No. 4);

| Samples take from | Intensity of the presence of immunoglobulins in $E_{\lambda 400\ nm} \times 10^3$ measured by using goat antibodies against*: | | | |
|---|---|---|---|---|
| | IgG | | | |
| Patient No. 4 | Fab-fragments | Fc-fragments | IgA | IgM |
| Protein A extraction: | | | | |
| of 1 µg human IgG** | 424 | 317 | n/d | n/d |
| of 3 µg human IgG** | 1211 | 1009 | n/d | n/d |
| 10 µg protein of PBS extract, Treated by Protein A*** | 890 | 296 | 185 | 256 |
| and subsequently by protein L*** | 742 | 262 | 324 | 411 |
| 10 µg protein of 1% Triton X-100 homogenate, treated by protein A*** | 622 | 103 | 122 | 11 |
| and subsequently by protein L*** | 318 | 19 | 157 | 0 | n/d—not determined;
*the dilutions of anti-IgG, -IgA, and -IgM conjugates were adjusted to equalise their differences in the absorption of 1 µg of the commercial samples of their antigens;
**commercial preparations;
***50 µl of protein A and protein L were used.

A further indication of the potential damage of immunoglobulins in these samples is derived from a comparison of the ratio between Fab and Fc portions of IgG. For the intact protein, under the conditions of the experiment and for the particular reagents used, this ratio was 55-57% for Fab and 43-45% for Fc. In PBS extracts the contribution of the latter portion was only 25-26% in the total mass of IgG which was equally presented on both protein A and protein L reagents. This imbalance was deeper developed in the homogenate of the lesion. Protein A extracted IgG which contained only 14% of Fc portions, but their level on the subsequently used protein L reagent was even lower, 5.6%.

The comparison of the immunoglobulin profile of the lesion with such of the plasma from the same patient is given in the Table 2. The analysis of PBS extract detected the accumulation of IgM on the surface of the lesion in 2.3 times higher than the level of this protein in circulating plasma. The other interesting observation was the certain elevation of IgG1 fraction in this extract on the background of the significant reduction of subclasses of IgG. Furthermore, this elevation in the lesion homogenate was even higher and the concentration of IgG1 was 1.6 higher than in the plasma. At the same time the presence there of other subclasses of IgG together with the second major immunoglobulin of PBS extract, IgM, was almost at trace level or undetectable.

TABLE 2

Content of immunoglobulins and their composition in the plasma and aorta wall of patient No. 4.

| | Samples, 10 µg of protein from: | | |
|---|---|---|---|
| Immunoglobulins | Plasma | Surface of the advanced atherosclerotic lesion (PBS extract) | Advanced atherosclerotic lesion itself (1% Triton X-100 homogenate) |
| Content, µg | 2.35 (100%) | 4.68 (100%) | 1.83 (100%) |
| Profile, µg | | | |
| IgG (total) | 1.72 (73.3%) | 3.09 (66.0%) | 1,44 (78.7%) |
| IgG1 | 1.13 (48.1%) | 2.56 (54.7%) | 1.41 (77.0%) |
| IgG2 | 0.377 (16.0%) | 0.411 (8.8%) | 0.033 (1.8%) |
| IgG3 | 0.126 (5.4%) | 0.049 (1.0%) | 0 |
| IgG4 | 0.063 (2.7%) | 0.065 (1.4%) | 0 |
| IgA | 0.430 (18.3%) | 0.688 (14.7%) | 0.377 (20.6%) |
| IgM | 0.195 (8.3%) | 0.901 (19.3%) | 0.0149 (0.8%) |

Example 2

Immunoglobulin Damage in IAM

Molecules of IgG interact with protein A via their Fc portion. Therefore the presence of the fraction of IgG which was not involved in this interaction could be considered 'disabled'. The ratio between IgG attached to the protein L reagent and the total amount of this protein bound by both the protein A and protein L reagents was used as a measure of the degree of this 'disability'. Following this, the damaged IgG was on the surface of the lesion 12.9 and inside the lesion 9.4 times higher than for the protein circulating in the plasma (Table 3).

TABLE 3

Distribution of 'disabled' IgGs which were unable to interact with protein A, and the degree of IgG fragmentation in human atherosclerosis;

| | | Fragmented IgG | |
|---|---|---|---|
| Entity | 'Disabled' Fc-IgG | on protein A reagent | on protein L reagent |
| Plasma | 81/2355 = 3.4% | 2.8% | n/d |
| Surface of atherosclerotic advanced lesion (PBS extract) | 1004/2290 = 44% | 58% | 55% |
| Core of atherosclerotic advanced lesion (1% Triton X-100 extract) | 337/1062 = 32% | 79% | 92% | n/d—not determined; the principles of the calculation of both parameters are given in the text.

The change in the balance between Fab and Fc portions in the analysed lesion extracts could be explained by the presence of the fragments of IgG therein. The Fab/Fc ratio, under experimental conditions and with the particular reagents used, for the commercial standard of human IgG was 1.27±0.22. A level of the absorption of Fc portion in an analysed sample was multiplied by this coefficient. If it is assumed that IgG fragmentation occurs as a simple cut in the hinge region without any further modification of polypeptide chains of IgG affecting their antigenic properties, the obtained figure would reflect the amount of Fab for the uncleaved IgG. The ratio between the excessive amount of Fab and its total content was used as a measure of the immunoglobulin fragmentation. If in the plasma only 1 out of 36 molecules of IgG was fragmented, on the surface of the atherosclerotic lesion this type of damage affected every other of these molecules. In the core of this lesion 8 or 9 out of 10 of IgG were fragmented (Table 3). Protein L reacts only with κ chain of $V_L$ domain of Fab but not with λ chain which might be present in half of the human IgG. Thus the sorbent based on this protein L could not guarantee full absorption of all the damaged IgG or their fragments. Consequently the real degree of the degradation of these immunoglobulins in the analysed lesion samples was probably even higher.

The relative excess of Fab but not Fc fragments of IgG in the protein A extracts has required some explanation. It is known that protein A interacts with Fc portion of all subclasses of IgG and with $V_H$III domain of their Fab portion. Thus the excessive accumulation of the latter portion of IgG on the protein A reagent could belong to the fragments containing this particular domain. Alternatively, the same immune complex, which has been extracted (ALICs, for example), could contain more than one antibody. One of them was able to interact with protein A, another (others) could be just be a Fab fragment(s) attached to the same antigen. The other possibility, Fab fragments of IgG could be a part of the antigens or antigens themselves (the result of the cleavage of other IgG) and, therefore, would be present in 'an excessive' quantities in the protein A extract.

The occurring Fc portions of the fragmenting IgG would be effectively scavenged by the Fc-receptors of fire variety of cells either in the circulation or in the lesion itself. This would lead to the apparent dominant accumulation of Fab fragments, and that was observed in the analysed samples.

Example 3

Clinical Study of Immunoglobulin Fragmentation

The amount of protein extracted from sera of the patients by protein A (IgG associated material) was 14.8±1.93 mg/ml against 24.5±1.08 mg/ml (p<001) in the control group. This may indicate either a reduced level of IgG production and/or 'impairment' of the Fc-portion of these molecules which led to the reduction of their ability to interact with protein A.

The latter suggestion was confirmed by the dominant presence of Fab fragments relative to Fc ones in protein L extracts of the sera of the patient, which were preliminary exhausted by protein A (p<001). The Fab/Fc ratio in this group was 2,413±271/857±156 µg/ml=2.82. Conversely, in the control group the level of Fab fragments was slightly below than Fc fragments (p>0.05) and was 1,579±188/1,862±259 µg/ml=0.88.

Individual analysis revealed that excess of Fab above Fc in protein L extracts is a quite consistent feature in patients' sera, being observed in 20 cases out of 21 or more than 95%. In the control group this phenomenon was observed only in 4 cases or in 19%.

So far, based on this limited study and on these particular groups of people, it is possible to conclude that IgG fragmentation/impairments happens not only in an arterial wall in atherosclerosis but also in the blood stream. It seems that tins phenomenon is a highly frequent feature in patients with clinical complications of atherosclerosis (at least much more common than hypocholesterolemia). This would suggest that the measurement of IgG attachment to protein A and/or Fab presence in protein L extracts could be new leading markers for this disease today.

| Groups | IgG extracted from serum by saturated amount of protein A, in µg/ml | IgG fragments attached to protein L, in µg/ml | | Total cholesterol in µg/ml |
|---|---|---|---|---|
| | | Fab | Fc | |
| Patients: | | | | |
| 1) Ki | 14,512 | 1,521 | 864 | 1,063 |
| 2) Pi | 17,788 | 968 | 899 | 1,402 |
| 3) Ci | 13,384 | 1,348 | 0 | 1,723 |
| 4) Mi | 12,150 | 864 | 1,797 | 2,293 |
| 5) Chs | 23,264 | 3,906 | 1,796 | 1,686 |
| 6) Y | 26,624 | 1,417 | 35 | 1,782 |
| 7) Ba | 11,178 | 1,970 | 1,175 | 1,438 |
| 8) Yk | 5,267 | 2,765 | 104 | 2,197 |
| 9) O | 15,875 | 2,731 | 795 | 1,543 |
| 10) M | 18,061 | 4,424 | 1,175 | 1,519 |
| 11) Sh | 5,494 | 3,387 | 1,486 | 2,002 |
| 12) Pa | 2,480 | 4,182 | 2,143 | 1,199 |
| 13) D | 4,217 | 2,039 | 691 | 1,015 |
| 14) Ch | 3,029 | 2,869 | 1,106 | 2,129 |
| 15) K | 9,592 | 3,491 | 1,037 | 1,223 |
| 16) C | 23,990 | 3,353 | 760 | 1,572 |
| 17) Z | 22,030 | 2,422 | 759 | 1,754 |
| 18) G | 18,061 | 1,624 | 830 | 1,551 |
| 19) B | 20,306 | 2,108 | 1,797 | 1,693 |
| 20) A1 | 7,202 | — | — | 1,750 |
| 21) A2 | 42,611 | — | — | 1,601 |
| 22) 40i | 19,201 | 1,694 | 0 | 1,286 |
| 23) 60a | 18,605 | 1,555 | 0 | 2,122 |
| Control: | | | | |
| 1) 1 | 24,985 | 1,728 | 588 | 2,074 |
| 2) 2 | 23,700 | 1,175 | 1,123 | 2,182 |
| 3) 3 | 28,574 | 1,901 | 2,627 | 1,986 |
| 4) 4 | 23,426 | 1,313 | 1,901 | 2,002 |
| 5) 5 | 34,432 | 2,281 | 2,420 | 1,806 |
| 6) 6 | 22,331 | 1,797 | 2,418 | 2,038 |
| 7) 7 | 24,657 | 1,521 | 3,249 | 2,110 |
| 8) 8 | 22,256 | 2,419 | 2,834 | 1,902 |
| 9) 9 | 23,034 | 1,289 | 1,556 | 1,756 |
| 10) 10 | 27,219 | 1,994 | 2,788 | 1,638 |
| 11) 11 | 20,533 | 1,002 | 1,427 | 1,591 |
| 12) 12 | 31,178 | 2,211 | 2,903 | 1,704 |
| 13) 13 | 24,208 | — | — | 1,337 |
| 14) 14 | 21,016 | — | — | 1,932 |
| 15) 1a | 36,032 | 657 | 2,627 | 1,359 |
| 16) 2a | 23,500 | 3,422 | 3,249 | 1,607 |
| 17) 3a | 14,975 | 2,039 | 1,659 | 1,714 |
| 18) 4a | 26,366 | 1,694 | 2,143 | 1,510 |
| 19) 5a | 28,361 | 35 | 0 | 1,516 |
| 20) 6a | 30,591 | 3,214 | 1,037 | 1,475 |
| 21) 7a | 24,499 | 728 | 2,558 | 1,480 |
| 22) 8a | 40,702 | 0 | 0 | 1,592 |
| 23) 9a | 54,210 | 724 | 0 | 2,030 |

Example 4

Nosocomial (Hospital Acquired) Pneumonia

The frequency of nosocomial pneumonia in the developed world for patients in hospitals (not for the surgical operation) is 0.2-0.5%.

Our survey of the three major hospitals in Russia (Rostov-na-Donu) found that the frequency of nosocomial pneumonia for patients with acute myocardial infarction was between 2.4% and 5.9% (table 5 below). The number of cases of this infection, for these hospitals, for the same period of time, for patients admitted with diseases other than cardiovascular pathology was 0.1-0.4%.

This difference of 6-14 times demonstrates a higher susceptibility of patients, with such clinical complication of atherosclerosis as myocardial infarction, towards nosocomial pneumonia. One possible explanation of this is the observation of the fact that more than ⅓ of the immunoglobulins class G is damaged in the plasma of these patients. Hence it can lead to a significant reduction of the anti-bacterial defence of the body.

TABLE 5

Frequency of nosocomial pneumonia in patients with myocardial infarction admitted to hospitals in Rostov-na-Donu, Russia between September 1999 and September 2000.

| Hospitals | Doctors who undertook the study | Acute myocardial infarction | |
|---|---|---|---|
| | | Number of patients | Cases of nosocomial pneumonia |
| Clinical Regional No1 Urgent Medicine | Alexey M. Petyaev Avia V. Vasil'eva and Anatoliy A. Stadnikov | 341 1,215 | 20 (5.9%) 31 (2.6%) |
| City Hospital No20 | Alla A, Zubkova | 328 | 8 (2.4%) |

Referring to the data from the clinical trial: 'The amount of protein extracted from the sera of patients by protein A (IgG associated material) was 14.8±1.93 mg/ml against 24.5±1.08 mg/ml (p<0.001) in the control group'. In other words, 60% of IgG was capable of being bound with protein A in the plasma of patients against 100% in the control.

Example 5

Post-Operative Infection Levels

The levels of post-operative infections in various surgery departments at the Rostov-na-Donu Clinical Hospital, Russia in 2000 were compared (see table 6). As artificial ventilation is a major factor in post-operative respiratory infections, only departments where artificial ventilation was used during all operations were chosen for the analysis. It was found that the level of infection amongst, patients undergoing cardio-vascular surgery was about 2-3 times higher than for patients operated on for other pathological conditions. These results indicate that IgG impairment may be one of the factors responsible for the higher level of susceptibility of patients with cardio-vascular pathology to post-operative infections.

TABLE 6

Frequency of post-operative infections in surgery departments of the Rostov-na-Donu Clinical Hospital, Russia in 2000.

| Department | No. of patients | Level of post-operative Infections |
|---|---|---|
| Gynecology | 1,784 | 1.01% (18 cases) |
| Urology | 1,052 | 0.95% (10 cases) |
| Traumatology | 1,810 | 0.16% (3 cases) |
| Jaw-face surgery | 825 | 1.21% (10 cases) |
| Neurosurgery | 654 | 1.53% (10 cases) |
| Thoraco-abdominal | 768 | 1.30% (14 cases) |
| Cardio-vascular surgery (of atherosclerotic occlusive disease) | 749 | 3.20% (24 cases) |

Example 6

In Vitro Digestion of Human IgG with Trypsin

It is known from the literature that trypsin can digest immunoglobulins and IgG in particular, splitting the latter into Fc and bivalent Fab portions. We have found that during this process only Fc but not Fab pails of IgG were affected. Under the conditions used, trypsin reduced binding by Fc to protein G by 50%, and damaged part(s) responsible for the binding of protein A in 2 out of 3 molecules of IgG (table 7). This indicates that the protein A binding site is more susceptible to trypsin digestion than the protein G binding site.

Using protein A to remove undamaged IgG from tested samples would therefore leave a higher level of damaged immunoglobulins in the remaining solution. As a result the subsequently used protein L sorbent would yield more Fc material. Hence, the use of protein A during the first stage of the test for the damaged IgG is preferable to the use of protein G.

TABLE 7

Effect of trypsin on the ability of human IgG to interact with different immuno-sorbents.

| | Human IgG attached to the sorbent, in µg/ml initial solution contained 1,000 µg/ml of IgG (100%) | |
|---|---|---|
| Sorbent used | +trypsin | −trypsin |
| Protein A | 135 ± 19.8 (13.5%) | 442 ± 22.1 (44.2%) |
| Protein L (added to the IgG Solution which was Preliminarily exhausted by Protein A) | 219 ± 16.6 (21.9%) | 200 ± 10.3 (20.0%) |
| Total amount of IgG bound by this procedure | 354 (35.4%) | 642 (64.2%) |
| Protein G | 240 ± 1.04 (24.0%) | 555 ± 3.46 (55.5%) |
| Complex of A/L proteins | 304 ± 0.67 (30.4%) | 502 ± 1.11 (50.2%) |

Example 7

In Vivo Comparison of IgG Fragmentation and Trypsin Activity

Two studies were carried out, in Russia and Norway respectively. In each study serum samples were taken from healthy volunteers and patients with atherosclerotic complications of atherosclerosis. The levels of IgG damage and trypsin activity were measured, to determine if there was any correlation.

For the Russian study, since it was found that the Fab portion of IgG is not affected by trypsin, the main focus was on an estimation of the relative amount of Fc-IgG material in the tested sera (once they were exhausted by protein A treatment). Therefore all samples were equalised on Fab concentration. In the control group there was 18.7±0.63 mg of Fab material per tested sample, and in the patient group there was 18.9±0.31 mg. The results of the study are shown in table 8. It was found that the level of IgG fragmentation/damage was significantly higher in the patients' sera than in the control samples, as previously demonstrated. However, the patient's sera also had a 2-fold higher level of trypsin activity than the control samples. The results showed that there was a statistically significant direct correlation (p<0.05) between IgG fragmentation and trypsin activity (FIG. 1).

Figure 2:
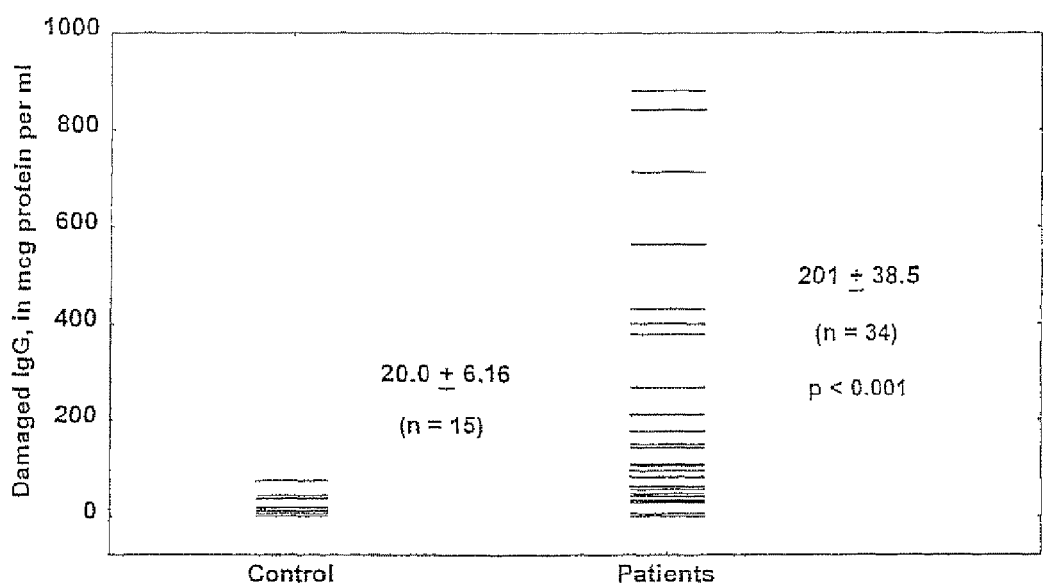
FIG. 2 shows a comparison of the level of damaged or fragmented IgG between patient and control groups in the Norwegian study. This parameter is expressed as the amount of protein L bound-IgG with an undetectable Fc portion, calculated as a difference in the concentration between Fab and Fc fragments associated with the sorbent. Undamaged IgG was removed by a saturating amount of protein A.
Figure 3:
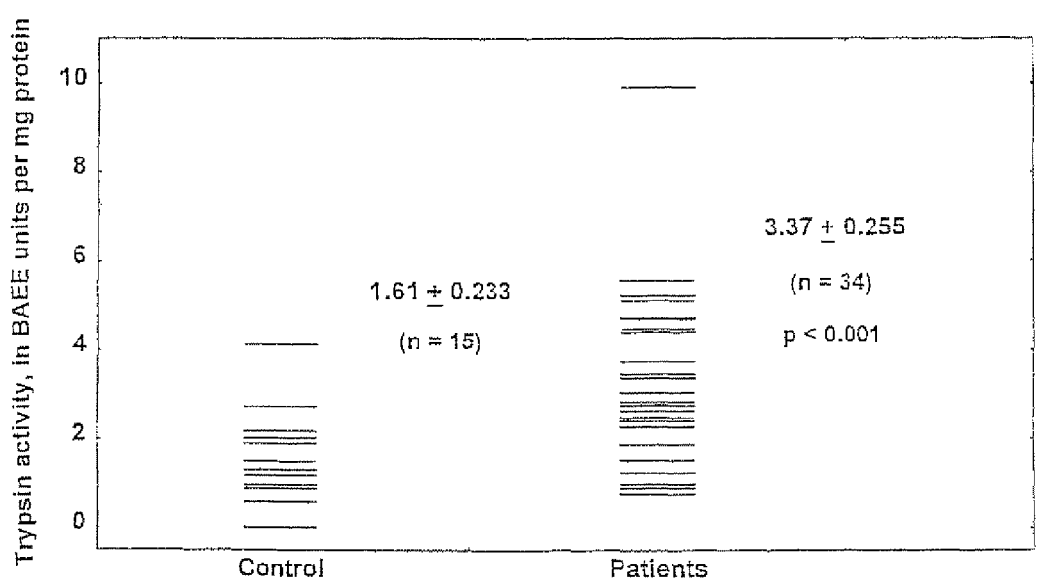
FIG. 3 shows a comparison of the trypsin activity of the serum samples from the patient and control groups of the Norwegian study.
Figure 4:
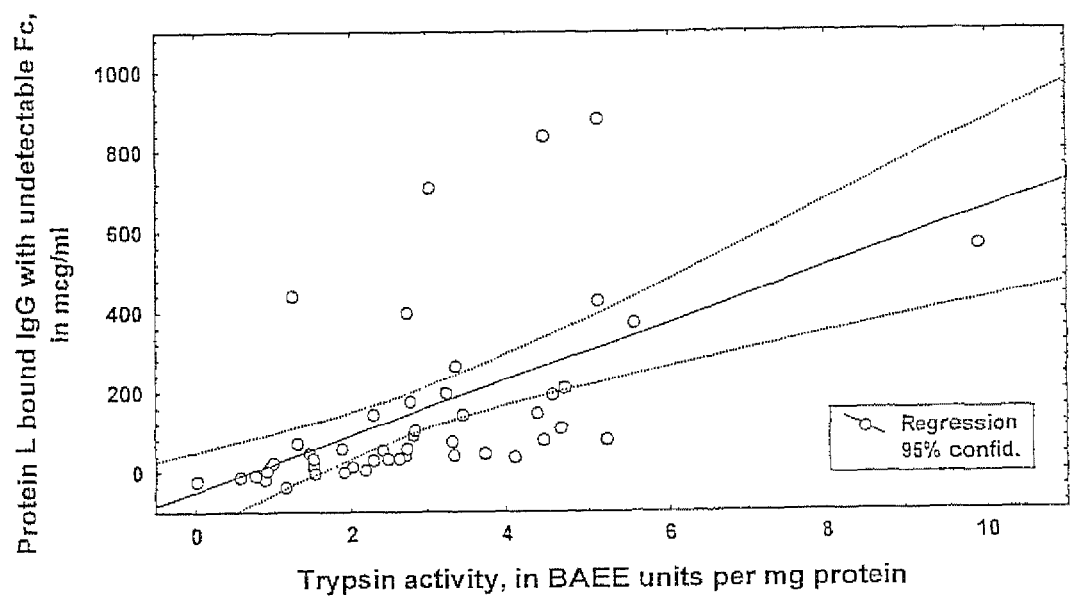
FIG. 4 shows the correlation between the level of trypsin activity and the level of protein L bound-IgG with undetectable Fc portion (casewise MD deletion, r=0.56379).

In the Norwegian study, the level of IgG damage was measured in terms of amount of protein L bound-IgG with undetectable Fc fragments. The ages, trypsin activity and the level of IgG damage in the sera of the patient and control groups are presented in table 9. These comparisons show that the level of the damaged IgG attached to the protein L was more than 9-fold higher in the patient sera than in the healthy control, p<0.001 (FIG. 2). This was accompanied by a 2-fold increase in the trypsin activity in the sera of the patients in comparison with the control (FIG. 3). A correlation analysis showed that these two parameters have a significant positive correlation with each other, r=0.5638 (FIG. 4), which was slightly weaker than in the Russian study (r=0.6384).

This correlation indicates that increased activity of trypsin can be considered as one of the factors responsible for the loss of the detectable Fc portion of IgG in atherosclerosis. In the Norwegian trial protein L bound damaged IgG was found in about 79% of the analysed patient samples and in 20% of the control samples. These results were close to the ones obtained on the Russian patients (table 10). These results demonstrate a significant diagnostic value of the measurement of the fragmented/damaged IgG bound to the protein L as a non-specific marker of chronic inflammatory conditions to which atherosclerosis belongs.

TABLE 8

Russian study. Comparison of IgG fragmentation and trypsin activity in serum samples.

| Tested group | Fc parts of human IgG attached to protein L, in µg | Trypsin Activity, in BAEE* units per mg of protein |
|---|---|---|
| Control | | |
| M | 9.52 | 1.98 |
| M3 | 9.20 | 0.94 |
| K | 7.86 | 2.69 |
| K2 | 11.38 | 1.84 |
| K3 | 7.95 | 2.47 |
| K4 | 12.23 | 0.85 |
| K5 | 8.77 | 1.94 |
| K6 | 9.56 | 1.43 |
| K7 | 7.89 | 2.38 |
| K8 | 10.55 | 1.22 |

TABLE 8-continued

Russian study. Comparison of IgG fragmentation
and trypsin activity in serum samples.

| Tested group | Fc parts of human IgG attached to protein L, in μg | Trypsin Activity, in BAEE* units per mg of protein |
|---|---|---|
| | 9.49 ± 0.401 (n = 10) | 1.77 ± 0.223 (n = 10) |
| Patients | | |
| 1 | 8.56 | 2.04 |
| 3 | 4.55 | 3.00 |
| 4 | 6.62 | 3.10 |
| 5 | 7.45 | 2.55 |
| 6 | 0.21 | 2.74 |
| 7 | 9.52 | 2.52 |
| 8 | 0 | 3.15 |
| 9 | 6.08 | 2.50 |
| 10 | 3.31 | 3.75 |
| 11 | 7.45 | 3.58 |
| 12 | 4.45 | 3.47 |
| 13 | 0 | 3.32 |
| 14 | 1.65 | 2.57 |
| 15 | 0 | 2.51 |
| 16 | 2.07 | 2.67 |
| 17 | 0.82 | 2.72 |
| 18 | 3.10 | 2.57 |
| 19 | 2.79 | 2.64 |
| 20 | 7.32 | 2.67 |
| 21 | 1.24 | 2.41 |
| 22 | 1.65 | 3.48 |
| | 3.81 ± 0.691 (n = 22) | 3.44 ± 0.132 (n = 22) |
| | p < 0.001 | p < 0.001 |

*1 BAEE unit equals changes of optical density at λ 253 nm 1 min with Nα-Benzoyl-L-Arginine as substrate at pH 7.4 at 37° C.

TABLE 9

Norwegian study. Trypsin activity and IgG impairment/fragmentation
in the sera of the patient and control groups.
IgG standard = 40.1.

| Serum from: | Age | Trypsin activity in BAEE units* per mg protein | Protein L bound IgG with no Fc portion, in μg/ml |
|---|---|---|---|
| Control | | | |
| 1. | 40 | 2.01 | 12.2 |
| 2. | 38 | 1.89 | 0.2 |
| 3. | 43 | 2.17 | 4.8 |
| 4. | 48 | 0 | 0 |
| 5. | 46 | 1.49 | 9.7 |
| 6. | 50 | 1.46 | 47.0 |
| 7. | 54 | 0.95 | 16.7 |
| 8. | 41 | 2.71 | 42.3 |
| 9. | 50 | 4.11 | 39.0 |
| 10. | 47 | 1.15 | 0 |
| 11. | 42 | 1.30 | 74.2 |
| 12. | 65 | 1.49 | 18.4 |
| 13. | 50 | 1.49 | 35.9 |
| 14. | 41 | 0.57 | 0 |
| 15. | 39 | 0.88 | 0 |
| | | 1.61 ± 0.233 (n = 15) | 20.0 ± 6.16 (n = 15) |
| Patients | | | |
| 1. | 69 | 3.32 | 75.2 |
| 2. | 56 | 3.35 | 41.6 |
| 3. | 57 | 9.90 | 562 |
| 4. | 53 | 4.46 | 80.4 |
| 5. | 39 | 2.76 | 176 |
| 6. | 51 | 2.28 | 142 |
| 7. | 69 | 4.38 | 149 |
| 8. | 43 | 2.72 | 399 |
| 9. | 87 | 2.61 | 32.5 |
| 10. | 65 | 2.82 | 93.9 |
| 11. | 78 | 4.47 | 840 |
| 12. | 49 | 2.83 | 104 |
| 13. | 36 | 2.27 | 30.8 |
| 14. | 46 | 2.41 | 55.8 |
| 15. | 57 | 0.98 | 27.9 |
| 16. | 77 | 4.67 | 108 |
| 17. | 71 | 0.89 | 4.6 |
| 18. | 71 | 1.51 | 0 |
| 19. | 57 | 1.88 | 61.4 |
| 20. | 89 | 2.47 | 34.2 |
| 21. | 77 | 3.23 | 197 |
| 22. | 75 | 0.76 | 0 |
| 23. | 55 | 1.23 | 441 |
| 24. | 64 | 3.03 | 712 |
| 25. | 78 | 5.10 | 881 |
| 26. | 64 | 4.71 | 212 |
| 27. | 80 | 3.37 | 267 |
| 28. | 73 | 5.55 | 376 |
| 29. | 61 | 5.10 | 429 |
| 30. | 68 | 5.21 | 82.6 |
| 31. | 75 | 4.58 | 195 |
| 32. | 88 | 3.45 | 142 |
| 33. | 72 | 3.73 | 46.5 |
| 34. | 67 | 2.72 | 61.0 |
| | | 189 ± 37.4 (n = 34) | 3.37 ± 0.255 (n = 34) |
| | | p < 0.001 | p < 0.001 |

*1 BAEE unit equals changes of optical density at λ 253 mm 1 min with Nα-Benzoyl-L-Arginine as substrate at pH 7.4 at 37° C.

TABLE 10

Comparison of results obtained in the two studies.

| | Number of serum samples where protein L bound IgG was damaged | |
|---|---|---|
| Country of the study | Control | Patients |
| Norway | 20% (3 out of 15) | 79% (27 out of 34) |
| Russia | 19% (6 out of 31) | 87% (39 out of 45) |

Example 8

Effect of a Trypsin Inhibitor on IgG Damage During Surgery

Two groups of patients were tested, each comprising three 50-60 year old male patients selected from the patients in the Russian study described above. Before undergoing by-pass surgery, the average level of parameters such as binding of > immunoglobulins to protein A, amount of Fc portions of IgG attached to protein L and trypsin activity in the sera of the patients in both groups were similar (see table 11). In one group each patient received intravenously 20,000 U of Trasylol™ (proprietary name for aprotinin) one to two hours before the beginning of cardio-vascular surgery. This drug is a worldwide accepted trypsin/kallikrein inhibitor and is used as one of the key components of acute pancreatitis therapy.

One hour after the end of the operation the blood of these patients was taken and compared with the blood of the patients who had not received aprotinin. The results are presented in table 11.

In the control group, the operation procedure reduced the level of immunoglobulins able to interact with protein A sorbent almost by half. There was a 10-fold increase in the activity of trypsin in the sera of these patients accompanied by significant IgG damage in terms of the amount of Fc attached to protein L. By contrast, the pre-operative injection of a trypsin inhibitor seems to have prevented these profound changes caused by the operation. This indicates that trypsin is one of the main factors that cause IgG damage in cardio-vascular surgery. It also indicates that trypsin inhibitors may be useful in preventing IgG damage, particularly during surgery.

TABLE 11

Effect of Trasylol on IgG damage during cardio-vascular by-pass surgery.

| Tested Group | IgG attached to protein A, in mg/ml | | Fc parts of human IgG attached to protein L, in μg | | Trypsin activity, in BAEE units per mg of protein* | |
|---|---|---|---|---|---|---|
| | before operation | after operation | before operation | after operation | before operation | after operation |
| Control Patient: | | | | | | |
| 8 | 16.2 | 10.1 | 0 | 0 | 3.15 | 40.2 |
| 9 | 23.8 | 8.5 | 6.08 | 1.03 | 2.50 | 24.7 |
| 10 | 19.8 | 12.3 | 3.31 | 0.45 | 3.75 | 39.3 |
| | 19.9 ± 2.25 (n = 3) | 10.3 ± 1.16 (n = 3) $p < 0.02$ | 3.13 ± 1.8 (n = 3) | 0.49 ± 0.31 (n = 3) $p > 0.05$ | 3.13 ± 0.36 (n = 3) | 34.7 ± 5.83 (n = 3) $p < 0.01$ |
| +Trasylol Patient: | | | | | | |
| 11 | 18.4 | 18.7 | 7.45 | 5.37 | 3.58 | 2.69 |
| 12 | 19.6 | 16.2 | 4.45 | 5.12 | 3.47 | 2.01 |
| 13 | 18.5 | 19.1 | 0 | 0 | 3.32 | 2.15 |
| | 18.8 ± 0.45 (n = 3) | 18.0 ± 1.05 (n = 3) $p > 0.05$ | 3.96 ± 2.3 (n = 3) | 3.49 ± 2.03 (n = 3) $p > 0.05$ | 3.46 ± 0.08 (n = 3) | 2.28 ± 0.23 (n = 3) $p < 0.01$ |

*1 BAEE unit equals changes of optical density at λ 253 nm 1 min with Nα-Benzoyl-L-Arginine as substrate at pH 7.4 at 37° C.

I claim:

1. A method for the treatment of a patient who has suffered or is suffering from a disorder associated with elevated trypsin activity or other proteolytic activity, which is correlated with IgG fragmentation or modification, which method comprises the step of administering to the patient a therapeutically effective amount of a an inhibitor of trypsin or the other proteolytic enzyme.

2. A method according to claim 1, wherein the disorder is an inflammation, opportunistic infection or disruption of immunoglobulin metabolism.

3. A method according to claim 2, wherein the inflammation, opportunistic infection or disruption of immunoglobulin metabolism is atherosclerosis, angina, claudication, nosocomial pneumonia or infection following cardiovascular surgery.

4. A method according to claim 1, wherein the inhibitor of trypsin or the other proteolytic enzyme is aprotinin.

5. A method according to claim 1, wherein (i) the patient has suffered from a disorder associated with elevated trypsin activity, which is correlated with IgG fragmentation or modification, and (ii) the inhibitor of trypsin is administered.

6. A method according to claim 5, wherein the inhibitor of trypsin is aprotinin.

7. A method according to claim 1, wherein (i) the patient is suffering from a disorder associated with elevated trypsin activity, which is correlated with IgG fragmentation or modification, and (ii) the inhibitor of trypsin is administered.

8. A method according to claim 7, wherein the inhibitor of trypsin is aprotinin.

9. A method for the treatment of a patient who has suffered or is suffering from a disorder associated with elevated trypsin activity or other proteolytic activity, which is correlated with IgG fragmentation or modification, which method comprises the step of administering to the patient a therapeutically effective amount of an inhibitor of trypsin or the other proteolytic enzyme, wherein the disorder is an inflammation, opportunistic infection or disruption of immunoglobulin metabolism.

10. A method according to claim 9, wherein the inflammation, opportunistic infection or disruption of immunoglobulin metabolism is atherosclerosis, angina, claudication, nosocomial pneumonia or infection following cardiovascular surgery.

11. A method according to claim 9, wherein the inhibitor of trypsin or the other proteolytic enzyme is aprotinin.

12. A method according to claim 9, wherein (i) the patient has suffered from a disorder associated with elevated trypsin activity, which is correlated with IgG fragmentation or modification, and (ii) the trypsin inhibitor is administered.

13. A method according to claim 12, wherein the trypsin inhibitor is aprotinin.

14. A method according to claim 9, wherein (i) the patient is suffering from a disorder associated with elevated trypsin activity, which is correlated with IgG fragmentation or modification, and (ii) the trypsin inhibitor is administered.

15. A method according to claim 14, wherein the trypsin inhibitor is aprotinin.

* * * * *